(12) United States Patent
Fritz et al.

(10) Patent No.: US 8,652,214 B2
(45) Date of Patent: Feb. 18, 2014

(54) CARTILAGE REPLACEMENT IMPLANT AND METHOD FOR PRODUCING A CARTILAGE REPLACEMENT IMPLANT

(75) Inventors: Juergen Fritz, Dusslingen (DE); Christoph Gaissmaier, Tuebingen (DE); Wilhelm K. Aicher, Ammerbuch (DE)

(73) Assignee: Tetec Tissue Engineering Technologies AG (DE)

( * ) Notice: Subject to any disclaimer, the term of this patent is extended or adjusted under 35 U.S.C. 154(b) by 0 days.

(21) Appl. No.: 13/156,954

(22) Filed: Jun. 9, 2011

(65) Prior Publication Data

US 2011/0238180 A1   Sep. 29, 2011

Related U.S. Application Data

(60) Division of application No. 11/402,308, filed on Apr. 10, 2006, now Pat. No. 8,231,685, which is a continuation of application No. PCT/EP2004/011240, filed on Oct. 8, 2004.

(30) Foreign Application Priority Data

Oct. 13, 2003 (DE) .................................. 103 48 219

(51) Int. Cl.
 *A61F 2/28* (2006.01)
(52) U.S. Cl.
 USPC ........................ 623/23.57; 606/151
(58) Field of Classification Search
 USPC .................. 623/14.12, 14.13, 23.76
 See application file for complete search history.

(56) References Cited

U.S. PATENT DOCUMENTS

| | | | |
|---|---|---|---|
| 4,846,835 A | 7/1989 | Grande | 128/898 |
| 5,084,051 A | 1/1992 | Törmäläet al. | 606/77 |
| 6,013,853 A | 1/2000 | Athanasiou et al. | 623/11 |
| 6,080,194 A | 6/2000 | Pachence et al. | 623/18 |
| 6,319,712 B1 | 11/2001 | Meenen et al. | 435/395 |

(Continued)

FOREIGN PATENT DOCUMENTS

| | | | |
|---|---|---|---|
| DE | 693 07 299 | 4/1997 | |
| DE | 197 21 661 | 11/1998 | A61L 27/00 |

(Continued)

OTHER PUBLICATIONS

Cherubino, P. et al.,"Autologous Chondrocyte Implantation Using a Bilayer Collagen Membrane: A Preliminary Report", Journal of Orthopaedic Surgery (Hong Kong), Jun. 2003, vol. 11, No. 1, pp. 10-15 XP002310328.

(Continued)

*Primary Examiner* — David Isabella
*Assistant Examiner* — Ann Schillinger
(74) *Attorney, Agent, or Firm* — DLA Piper LLP (US)

(57) ABSTRACT

To improve a cartilage replacement implant for the biological regeneration of a damaged cartilage area of articular cartilage in the human body, comprising a cell carrier which has a defect-contacting surface for placement on the damaged cartilage area and is formed and designed for colonization with human cells, so that after implantation of the cartilage replacement implant, formation of a gap between adjacent contact surfaces of the implant and surrounding recipient tissue is minimized, it is proposed that the cell carrier rest with surface-to-surface contact on a carrier and be joined to the carrier at a cell carrier surface that faces away from the defect-contacting surface. A method for producing a cartilage replacement implant is also proposed.

3 Claims, 3 Drawing Sheets

(56) References Cited

U.S. PATENT DOCUMENTS

| | | | |
|---|---|---|---|
| 6,398,814 B1 | 6/2002 | Paasimaa et al. | 623/23.51 |
| 7,914,808 B2 * | 3/2011 | Malaviya et al. | 424/423 |
| 2002/0082220 A1 * | 6/2002 | Hoemann et al. | 514/21 |
| 2003/0033022 A1 * | 2/2003 | Plouhar et al. | 623/23.57 |

FOREIGN PATENT DOCUMENTS

| | | | |
|---|---|---|---|
| DE | 198 03 673 | 8/1999 | |
| DE | 199 50 406 | 5/2001 | |
| EP | 1 273 312 | 1/2003 | |
| WO | 88/03417 | 5/1988 | |
| WO | 98/52498 | 11/1998 | A61F 2/28 |
| WO | 01/30276 | 5/2001 | A61F 2/30 |

OTHER PUBLICATIONS

Cui, Yan Lu, et al., "Biomimetic Surface Modification of Poly(L-lactic acid) with Chitosan and its Effects on Articular Chondrocytes in Vitro", Biomaterials, Elsevier Science Publishers BV., Barking, GB, vol. 24, No. 21, Sep. 2003, pp. 3859-3868, XP004431167.

Ma Zuwei, et al., "Immobilization of Natural Macromolecules on Poly-L-Lactic Acid Membrane Surface in Order to Improve its Cytocompatibility", Journal of Biomedical Materials Research, 2002, vol. 63, No. 6, pp. 838-847, XP002310329.

SFA Arthroskopie Aktuell; "Biomaterialien fur die Transplantation Chondrogener Zellen zur Biologischen Rekonstruktion Artikulärer Knorpeldefekte", vol. 16, Oct. 2, 2003, pp. 4-14, XP009041180.

* cited by examiner

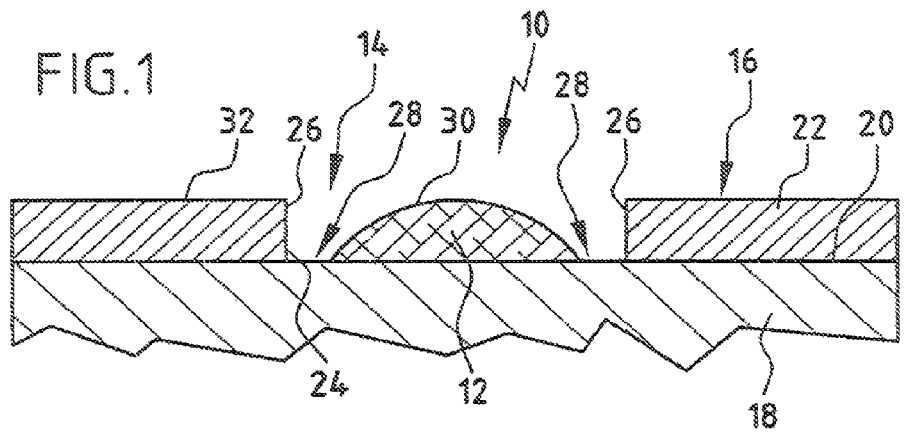
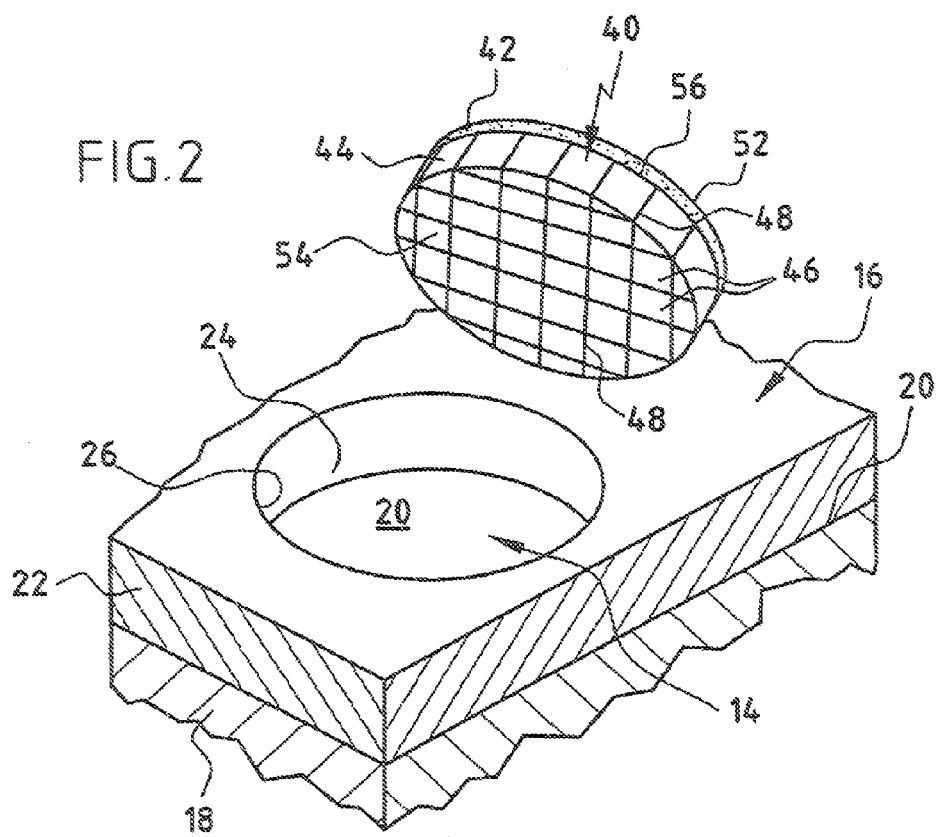

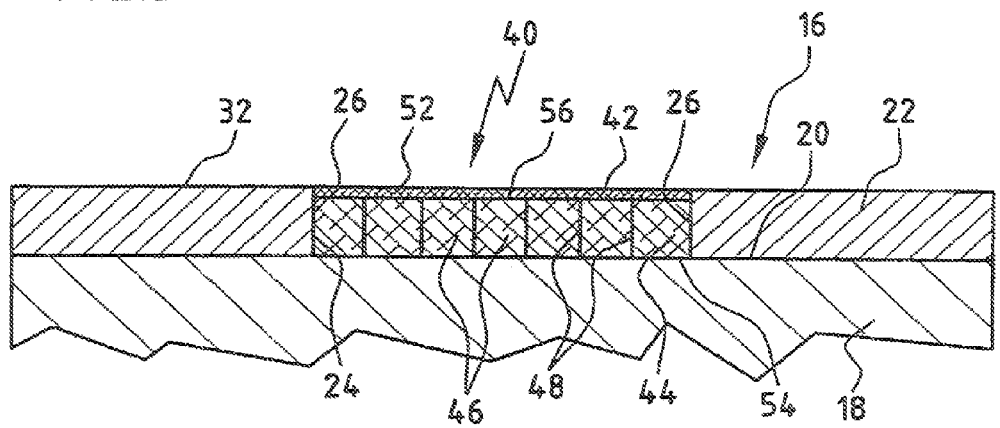
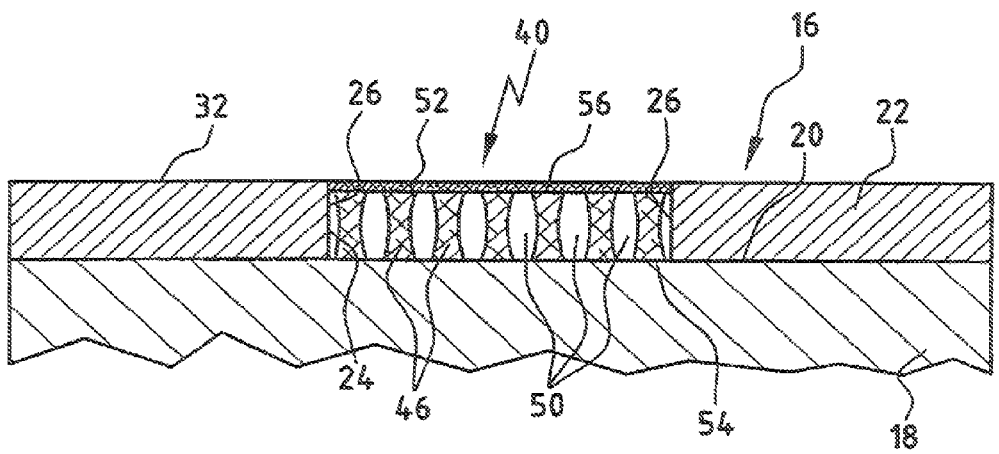

US 8,652,214 B2

CARTILAGE REPLACEMENT IMPLANT AND METHOD FOR PRODUCING A CARTILAGE REPLACEMENT IMPLANT

RELATED APPLICATIONS

This application is a divisional of U.S. Ser. No. 11/402,308 filed on Apr. 10, 2006 which is a continuation of international application number PCT/EP2004/011240 filed on Oct. 8, 2004 and claims priority of German application number 103 48 219.9 filed on Oct. 13, 2003.

The present disclosure relates to the subject matter disclosed in international application number PCT/EP2004/011240 of Oct. 8, 2004 and German application number 103 48 219.9 of Oct. 13, 2003, which are incorporated herein by reference in their entirety and for all purposes.

BACKGROUND OF THE INVENTION

The invention relates to a cartilage replacement implant for the biological regeneration of a damaged cartilage area of articular cartilage in the human body, comprising a cell carrier which has a defect-contacting surface for placement on the damaged cartilage area and is formed and designed for colonization with human cells.

The invention further relates to a method for producing a cartilage replacement implant for the biological regeneration of damaged articular cartilage in the human body, wherein a cell carrier is used, which has a defect-contacting surface for placement on the damaged cartilage area and is formed and designed for colonization with human cells.

Cartilage replacement implants of the kind described at the outset are used without or after previous inoculation with the body's own cells for the reconstruction of cartilage defects in articular cartilage in the human body. Biomaterials which can be resorbed by the body are usually selected.

However, with biomaterials for a cell-free implantation with or without growth factors or in the carrier-coupled transplantation of cells, for example, chondrocytes obtained and proliferated from the body's own cells or mesenchymal stem cells, into a tissue defect, for example, a damaged cartilage area, there is the problem that in the course of their resorption, the biomaterials used develop the tendency to contract. Such a contraction and hence shrinkage of biomaterials can often be observed after their contact with cells both in vitro and in vivo and is caused, above all, by contractile elements of seeded or immigrated cells. An undesired consequence of this is that upon commencement of resorption of the biomaterials, the mechanical stability of the implant structures diminishes and the contraction caused by the cells results in a considerable change in shape and volume contraction of the biomaterial.

In the biological regeneration of different tissues of the locomotor system and, in particular, in the reconstruction of structures under pressure load, for example, the articular cartilage in the knee, the annulus fibrosus of the intervertebral disc or the nucleus pulposus of the intervertebral disc, it is, however, of great importance that, as far as possible, a gap-free fusion should take place between the regenerated material resulting from the replacement implant and the healthy surrounding structures of the recipient site, i.e., of the defective tissue area. Gap formations between the regenerated material and healthy surrounding structures of the recipient site, or, in other words, the failure of implant and recipient structures to grow together in a stable manner, may, however, endanger the functional results of the biological reconstruction in the course of further developments. For example, a gap formation in the area of transition between local cartilage and replacement implant at cartilage level constitutes a biomechanical weak point and often forms the starting point of further cartilage degeneration.

The object underlying the present invention is, therefore, to so improve a cartilage replacement implant and a method for producing a cartilage replacement implant that gap formation is minimized between adjacent contact surfaces of the implant and surrounding recipient tissue after implantation of the cartilage replacement implant.

SUMMARY OF THE INVENTION

This object is accomplished in a cartilage replacement implant of the kind described at the outset, in accordance with the invention, in that the cell carrier rests with surface-to-surface contact on a carrier and is joined to the carrier at a cell carrier surface that faces away from the defect-contacting surface.

The cell carrier, which can be inoculated with cells before or after implantation, is resorbed in the desired manner by the body, but it contracts in the known way. A contraction of the entire cartilage replacement implant can, however, be avoided by use of the carrier, which can maintain its shape and structure longer than the cell carrier. Gap formation between the cartilage replacement implant and surrounding, undamaged cartilage tissue is thereby prevented or at least minimized. In this way, biomechanical weak points are avoided in the area of transition between implant and remaining body tissue.

To avoid rejection by the body after insertion of the cartilage replacement implant, it may be expedient for the cartilage replacement implant to be made from at least one biocompatible material.

If the cell carrier is inoculated with, for example, the body's own cells prior to implantation, it is desirable for the implant to be removable after the body's own cells have grown in. This can be achieved particularly easily in an advantageous manner by the at least one biocompatible material being resorbable.

In principle, it is conceivable to produce the cell carrier and the carrier from identical materials, in particular, biocompatible materials. They could then differ, for example, solely by way of their structure. It is, however, advantageous for the cell carrier and the carrier to be made from different biocompatible materials. This enables optimum formation of the cell carrier for reception of cells for regeneration of the defect and of the carrier for stabilization of the cell carrier connected to it and for avoidance of gap formations at the edge of the implant.

The overall stability of the implant is increased and gap formation at the edge of the implant reduced or completely avoided when the cell carrier and the carrier have resorption times of different lengths.

It is advantageous for the resorption time of the carrier to be longer than the resorption time of the cell carrier. The stability of the implant can thereby be ensured also after resorption of the cell carrier has started.

The cell carrier and the carrier preferably have different resorption kinetics. For example, the implant can be made up so that the carrier is first resorbed very slowly, and an accelerated resorption of the carrier only commences after complete resorption of the cell carrier, which is resorbed quicker.

In order to provide a replacement which is as ideal as possible for a defective cartilage area, it is expedient for the carrier to be formed and designed so that it can be colonized with human cells. In this way, it is possible to colonize both the cell carrier and the carrier with cells, so that cell growth and growth of the implant to surrounding tissue are possible from all parts of the implant.

To enable optimum adaptation of the implant to a damaged cartilage area, it may be advantageous for the cell carrier to comprise at least two different cell carrier layers. These may differ, for example, with respect to the type of material used or with respect to their structure, so that they can also be optimally formed for inoculation with different cells.

In principle, it is conceivable to provide an implant comprising a cell carrier which is free of human cells. After its implantation, such an implant enables stem cells to be absorbed from the bone marrow by bleeding. However, in order to achieve particularly good ingrowth of the implant, the cell carrier may be inoculated with human cells.

Optimum reconstruction of the damaged cartilage area becomes possible when the human cells are chondrocytes that are cultured and proliferated from the body's own cells. Cells of that cell type which are most similar to the adjacent, healthy tissue in its differentiated form are thus incorporated into the defect. In this way, rejection by the body can virtually be excluded.

In accordance with a preferred embodiment of the invention, it may be provided that the cell carrier and the carrier have a different mechanical stability. Accordingly, either the cell carrier or the carrier can be mechanically more stable and contribute towards holding the implant together while it grows in.

It is expedient for the carrier to have a higher mechanical stability than the cell carrier. For example, the cell carrier can be optimized for reception of cells and, therefore, preferably have a mechanically more unstable structure. The mechanically more stable carrier then ensures the overall stability of the implant while it grows in.

In principle, it is conceivable for the cell carrier and the carrier to have identical moduli of elasticity. However, the cell carrier and the carrier preferably have different moduli of elasticity. In this way, stabilities of the cell carrier and the carrier can be specifically preset in the desired manner.

In order to obtain a particularly stable carrier, it is expedient for the modulus of elasticity of the carrier to be greater than the modulus of elasticity of the cell carrier. Thus, the shape of the implant is essentially predetermined by the more inelastic carrier.

Furthermore, it is conceivable for the carrier and the cell carrier to have an identical structure, for example, also a structure having the same density. It is, however, advantageous for the carrier to have a denser structure than the cell carrier. In this way, the cell carrier can absorb and incorporate cells particularly well. On the other hand, a denser structure of the carrier has the additional advantage that, depending on the density of the carrier, the carrier can seal the defective cartilage area off from the outside.

To prevent undesired loosening of the cell carrier from the carrier, it is advantageous for the cell carrier to be undetachably connected to the carrier. For example, the implant can then be prepared from a carrier/cell carrier structure for the implantation by, for example, being cut to size, with the cell carrier being unable to become detached from the carrier on account of the undetachable connection.

The cell carrier can be inoculated particularly well with cells, or it is suitable for the bleeding-in of stem cells, when it has a sponge-like structure.

The cell carrier preferably has a cell carrier layer thickness ranging from 0.3 mm to 3.5 mm. Defective cartilage areas of different depths can thus be filled out with the implant.

It is expedient for the cell carrier to have a cell carrier layer thickness ranging from 1.0 mm to 3.5 mm.

Depending on the depth of the defective cartilage area, it is advantageous for the carrier to have a carrier layer thickness ranging from 0.01 mm to 0.8 mm. Depending on the required stability and size of the defect site, implants with smaller or larger carrier layer thicknesses may be selected.

Furthermore, it is expedient for the carrier to have a carrier layer thickness ranging from 0.2 mm to 0.4 mm.

In accordance with a preferred embodiment of the invention, it may be provided that the cell carrier is made from a material having a pore width ranging from 30 μm to 500 μm Depending on the type of cartilage defect, for example, in dependence upon the joint affected, different pore widths may be selected so as to inoculate cells in an advantageous manner.

The cell carrier is preferably made from a material having a pore width ranging from 80 μm to 150 μm.

It is expedient for the carrier to be made from a porous material having a pore width of at most 20 μm. Perfusion of the cells through the carrier into the free joint space is thereby excluded. However, a transportation of substances in the joint fluid, which are required for feeding cells introduced into the cell carrier, through the carrier is ensured.

During the resorption of the cell carrier, tensile forces may arise, which cause a build-up of compressive forces in the carrier, which may result in an undulated warping of the entire implant. The risk of gap formation at the edges of the implant is thereby increased. It is, therefore, advantageous for the carrier to comprise at least two cell carrier elements which are independent of each other, and for each of the at least two cell carrier elements to be joined to the carrier. Such a division of the cell carrier forming a substructure of the implant into cell carrier elements or units, which, in particular, do not have to be completely joined to one another directly, results in only individual cell carrier elements contracting. In this way, the shrinkage, caused by the contraction, of the entire cell carrier as a unit and also of the entire implant can be prevented, so that the contact surfaces of implant and recipient structures surrounding the implant after implantation do not move away from one another. Rather, individual separating gaps between the cell carrier elements are enlarged by contraction of the individual cell carrier elements. Therefore, given a large number of cell carrier elements, a large number of separating gaps will be formed, which do not result in any overall shrinkage of the implant or any large gap formation at the edge of the implant and taken on their own are insignificant.

In order to prevent warping of the implant, as far as possible, it is expedient for the at least two cell carrier elements to have cell carrier element surfaces and for cell carrier element surfaces of adjacent cell carrier elements to border loosely on one another. It is thereby ensured that adjacent cell carrier elements are only joined to one another via the carrier, with there being no direct connection between adjacent cell carrier elements. Consequently, only individual cell carrier elements shrink, which does increase gaps between adjacent cell carrier elements, but minimizes a gap between the implant and tissue surrounding the implant.

In order that the gap will be kept as small as possible after resorption of the implant, it is advantageous for the at least two cell carrier elements to be separated by at least one cut gap made by cutting into a one-piece cell carrier.

In order, for example, to optimally fill out bent cartilage areas, it may be advantageous for the at least two cell carrier elements to be separated by at least one split and for the at least one split to have a width ranging from 0.1 mm to 0.8 mm.

The implant can thus be bent prior to insertion, whereby an effective gap width between adjacent cell carrier elements can be minimized.

It is advantageous for the at least one split to be filled up with a biocompatible, resorbable material. The implant can thus be inserted in a particularly compact form into the cartilage area.

In order to avoid warping of the implant in the above-described manner, i.e., formation of an undulating structure after commencement of resorption, in particular, of the cell carrier, it is expedient for the at least one cut gap or the at least one split to have a depth corresponding to at least half of the layer thickness of the cell carrier.

In principle, a large number of different biocompatible materials are suitable for production of the implant. It is, however, advantageous for the at least one biocompatible material to be a collagen non-woven material.

Furthermore, it may be expedient for the at least one biocompatible material to be a polymer, preferably a synthetic polymer.

A particularly good resorption of the implant is ensured when the at least one biocompatible material is gelatine.

Preferably, the at least one biocompatible material may also be a collagen gel.

Furthermore, it is conceivable for the at least one biocompatible material to be a chitin derivative.

It is advantageous for the at least one biocompatible material to be a hyaluronic acid derivative.

In order that the implant will be unable to become detached from the defect site in an undesired manner, it is advantageous for connection means to be provided for anchoring the implant to the defective cartilage area.

The implant can be anchored to the defective cartilage area particularly easily when the connection means comprise resorbable suture material. The implant can thus be sewn into the defect site.

Additionally or alternatively, the connection means may comprise at least one resorbable attachment pin. The implant can be secured at least temporarily to the defective cartilage area with the at least one attachment pin.

Additionally or alternatively, the connection means may comprise a biocompatible and resorbable adhesive. The use of an adhesive makes it possible to advantageously fix the implant over a large area to the edge of the natural cartilage. The resorption time of all possible connection means is preferably selected so that the connection means are only completely resorbed when a minimal growth of the implant into the defective cartilage area is ensured.

To make it easier for the body's own stem cells to bleed into the cell carrier, it may be expedient for the defect-contacting surface of the cell carrier to be perforated.

The object set at the outset is accomplished with a method of the kind described at the outset for producing a cartilage replacement implant, in accordance with the invention, in that the cell carrier is joined with surface-to-surface contact to a carrier at a cell carrier surface that faces away from the defect-contacting surface. It is also conceivable to select a uniform implant material and to process part of the material so that two different implant materials are formed, namely a cell carrier and a carrier. Both the joining of two different elements and the processing of a uniform element are particularly easy. The joining of two different elements has the additional advantage that different materials may be used in a simple way.

To facilitate growth of the implant into a defective cartilage area and to avoid rejection by the human body, it is advantageous for at least one biocompatible material to be used for producing the implant.

It is expedient for the cell carrier to be inoculated with human cells. The inoculating of the cell carrier with cells prior to implantation has the advantage that it can thereby be ensured that sufficient cell material will be implanted in the defective cartilage area. The bleeding-in of stem cells may involve the risk that insufficient cells will bleed in and thereby prevent optimum regeneration of the defective cartilage area.

Chondrocytes cultured and proliferated from the body's own cells are preferably used as human cells. Such cells are not rejected by the body and ensure a rapid build-up of new cartilage substance.

In order that the overall stability of the implant will be increased, it is advantageous for the cell carrier to be undetachably connected to the carrier.

Since the cell carrier may contract as a result of its resorption, i.e., suffer a loss in volume, it is proposed, in order to avoid formation of large contraction gaps in the edge area of the implant, that at least two cell carrier elements which are independent of each other be used for formation of the cell carrier, and that each of the at least two cell carrier elements be firmly joined to the carrier. In this way, the individual cell carrier elements may contract and shrink, which results in contraction gaps between adjacent cell carrier elements, but, all in all, these are each significantly smaller than a contraction gap forming in the edge area of the implant without the presence of cell carrier elements.

It is advantageous for the at least two cell carrier elements not to be directly connected to each other but only via the carrier. In this way, each cell carrier element may contract for itself, which results in only a local gap formation around one cell carrier element respectively, with the formation of a large and undesired contraction gap thereby being avoided. In addition, all contraction gaps between individual cell carrier elements are covered by the carrier, so that a continuous joint surface is, at any rate, ensured.

A cartilage replacement implant can be produced particularly easily when the at least two cell carrier elements are produced by at least one cut into a one-piece cell carrier, so that the at least two carrier elements are separated by at least one cut gap. For example, the cell carriers may be cut into with a sharp cutting tool, for example, a scalpel or the like, so that a cut gap of minimal width is formed.

In accordance with a preferred variant of the method, it may be provided that the at least two cell carrier elements are separated by at least one split having at least a width ranging from 0.1 mm to 0.8 mm. The formation of such a split makes it possible to also insert the implant into a bent area, and there again adjacent cell carrier elements can rest against one another.

To enable optimum and complete filling-out of the defective cartilage area, it is advantageous for the at least one split to be filled up with a biocompatible, resorbable material.

To avoid the formation of warping by tensile forces acting on the cell carrier as a result of its resorption, it is advantageous for the cell carrier to be cut into at least as far as half the layer thickness of the cell carrier in order to make the at least one cut gap or the at least one split. It is thereby ensured that individual cell carrier elements can contract locally, so that the contraction gaps do occur around each individual cell carrier element, but the implant as a whole remains in position, and the formation of a wide contraction gap is avoided in the edge area of the implant.

The object set at the outset is further accomplished by a method for treating a traumatic or inflammatory, degenerated cartilage defect in a cartilage in the human body, in accordance with the invention, in that one of the above-described cartilage replacement implants is inserted into the cartilage defect. It is thereby ensured that in the edge area of the implant, after implantation and resorption thereof, there is no formation of a large contraction gap that, as possible biomechanical weak point, might constitute the starting point of further cartilage degeneration.

To ensure that the implant retains its position at the defective cartilage area, it is advantageous for the cartilage replacement implant to be anchored to the cartilage defect with resorbable suture material.

Alternatively or additionally, the cartilage replacement implant can be anchored to the cartilage defect by fixing it in place with at least one resorbable attachment pin. Such attachment pins facilitate the suturing of the implant to the defective cartilage area.

To ensure that the implant is held optimally at the defective cartilage area, it is expedient for the cartilage replacement implant to be anchored to the cartilage defect by bonding it with a biocompatible and resorbable adhesive. It can thus be ensured that the cell carrier is secured, on the one hand, to the carrier and, on the other hand, to the defective cartilage area.

The method according to the invention is suitable for restoring defective cartilage areas in the knee, in the intervertebral disc or in any other joint of the human body.

In principle, it is advantageous for the implant to be inoculated with cartilage cells, for example, chondrocytes cultured and proliferated from the body's own cells, prior to implantation. It is, however, expedient for the cartilage replacement implant to be implanted without previous colonization of the cell carrier or the carrier, so as to enable stem cells to bleed from the bone marrow into the cartilage replacement implant. Stem cells that have bled in can then transmute, for example, into cartilage cells and contribute towards the regeneration of the defective cartilage area.

Preferably, a subchondral plate on the bone is perforated prior to insertion of the cartilage replacement implant. In particular, when a cartilage replacement implant is used, which comprises a cell carrier into which no cells were implanted prior to implantation of the implant, a perforation of the subchondral plate on the bone, i.e., of the bone surface against which a defect-contacting surface of the cell carrier rests after implantation, allows the body's own stem cells to bleed into the cell carrier due to bleeding caused by the perforation.

The following description of preferred embodiments of the invention serves in conjunction with the drawings for further explanation.

BRIEF DESCRIPTION OF THE DRAWINGS

FIG. 1 shows a cross section through a grown-in cartilage replacement implant, as it is known from the prior art;

FIG. 2 shows a perspective view of a first embodiment of an inventive implant prior to insertion into a defective cartilage area;

FIG. 3 shows a longitudinal sectional view through the implant shown in FIG. 2, inserted in the defective cartilage area;

FIG. 4 shows a sectional view similar to FIG. 3 after resorption of the cell carrier layer has started.

DETAILED DESCRIPTION OF THE INVENTION

Figure 5:
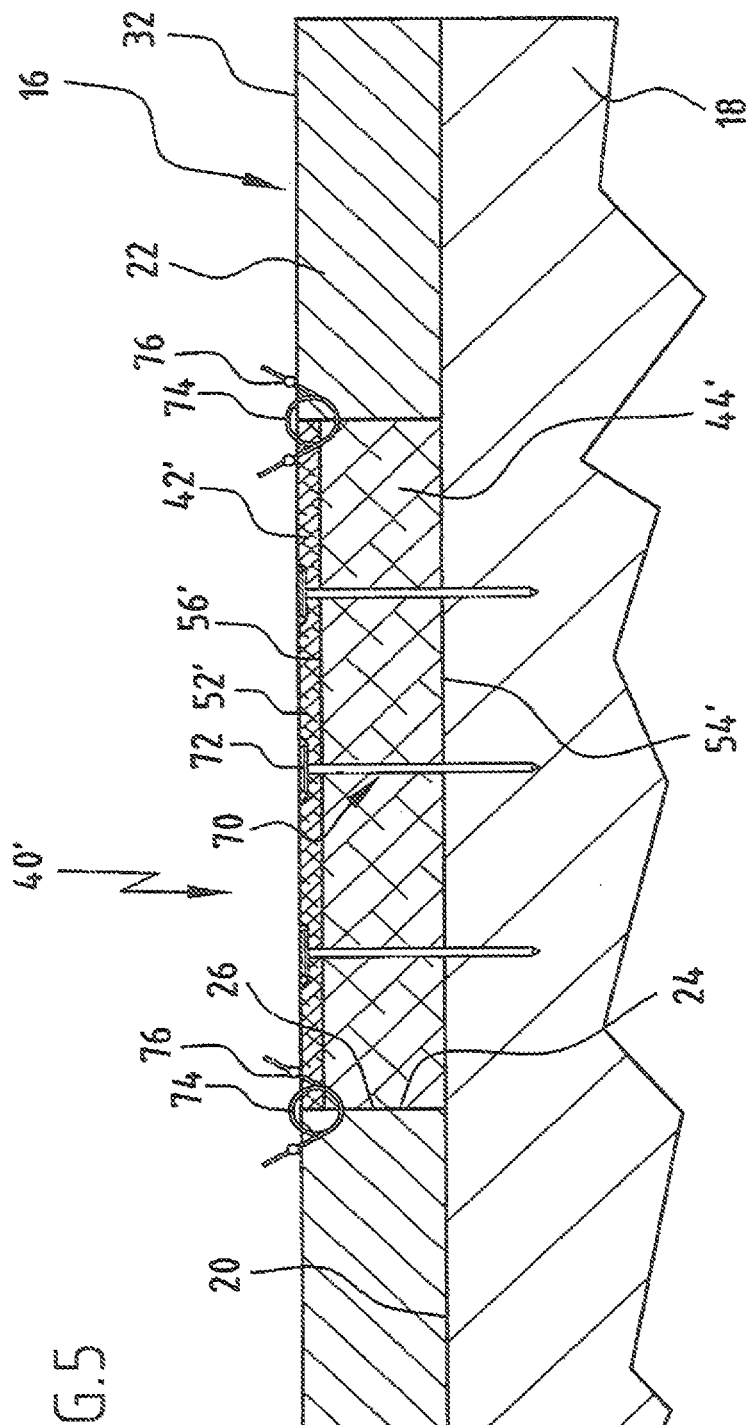
FIG. 5 shows a sectional view similar to FIG. 3 through a second embodiment of an inventive implant with pins as anchoring elements for anchoring the implant in the defect.

FIG. 1 shows a cartilage replacement implant 10, as it is known from the prior art. It consists of only one cell carrier 12, which may be inoculated with cells or not prior to implantation. In FIG. 1, the cartilage replacement implant 10 is inserted into a cartilage defect 14 of an otherwise intact cartilage area 16 of a joint in the human body. The cartilage area 16 is formed by a bone 18 and articular cartilage 22 covering the surface 20 thereof. For the sake of simplicity, the structure of the bone 18 and the articular cartilage 22 covering the surface 20 thereof is represented as a two-layer model. In nature, the transition from bone to cartilage usually occurs via a gradient of several millimeters in length. The cartilage defect 14 may have been caused by, for example, traumatic or inflammatory, degenerative processes. As shown schematically in FIG. 1, the cartilage defect 14 forms a gap in the cartilage area 16, which is delimited at the sides by cartilage edges 26 of the intact cartilage area 16. The cartilage edges 26 are substantially smooth and result from removal of degenerative cartilage prior to insertion of the cartilage replacement implant 10.

FIG. 1 shows the replacement implant after it has grown in, i.e., after at least partial resorption of the implant. As a result of the contraction, the cell carrier forms an arched cell carrier surface 30 facing away from the bone 18. The cell carrier 12 contracts as a whole, which results in formation of a contraction gap 28 surrounding the cell carrier 12. The contraction gap 28 forms between the cartilage edges 26 and the cell carrier surface 30 of the cell carrier 12 pointing in the direction of these. Such a persistent gap formation in the area of transition between intact cartilage area 16 and cartilage replacement implant 10, as biomechanical weak point, often forms the starting point of further cartilage degeneration.

For the sake of simplicity, identical reference numerals are used to describe the cartilage defect in the following Figures.

FIG. 2 shows an inventive cartilage replacement implant, which is generally designated by reference numeral 40. Prior to implantation, it is substantially disc-shaped and has an outer contour which is adapted to the cartilage defect 14, in order to fill out the space 24 in the cartilage area 16 as completely as possible.

The cartilage replacement implant 40 is of two-phase configuration, i.e., it comprises a carrier layer 42 and a cell carrier layer 44 joined with surface-to-surface contact thereto. The carrier layer 42 is thinner than the cell carrier layer 44 and typically has a thickness of from 0.01 mm to 0.8 mm. The thickness of the cell carrier layer ranges from 0.3 mm to 3.5 mm. Layer thicknesses of the carrier layer 42 and the cell carrier layer 44 are typically selected in dependence upon the depth of the cartilage defect 14.

Both the carrier layer 42 and the cell carrier layer 44 are made from a biocompatible resorbable material. The mechanical stability of the carrier layer 42 is greater than that of the cell carrier layer 44. Similarly, the resorption time of the carrier layer 42 is longer than that of the cell carrier layer 44. In addition, the carrier layer 42 has a denser structure than the cell carrier layer 44. The latter is of sponge-like construction and has a pore width of from 30 µm to 500 µm. The carrier layer 42, on the other hand, has pore widths of at most 20 µm.

The macroscopic structure of the cell carrier layer 44 is defined by a large number of block-shaped or cube-shaped cell carrier elements in the form of units 46, which are formed by cutting into the cell carrier layer in the direction towards the carrier layer 42. The units 46 are, therefore, separated from one another by cut gaps 48 and are only joined to one another via the carrier layer 42. For example, the individual units 46 may be adhesively joined to the carrier layer 42.

FIG. 3 shows the cartilage replacement implant 40 inserted into the cartilage defect 14 in longitudinal section. It fills out the space 24 practically completely. A bone-contacting surface 54, facing away from the carrier layer 42, of the cell carrier layer 44 lies essentially directly on the surface 20 of the bone 18.

After resorption of the cell carrier layer 44 has started, the individual units 46 contract, which results in enlargement of the cut gaps 48 to contraction gaps 50. Owing to the fixed connection of the cell carrier layer 44 to the carrier layer 42 and growth of the units 46 onto the surface 20 of the bone 18, the units 46 assume a cooling-tower-like shape. Owing to the greater mechanical stability of the carrier layer 42, it does, however, maintain its original shape for a considerably longer time than the cell carrier layer 44, so that the cell carrier surface 52, which completes the cartilage surface 32 of the cartilage area 16 in the area of the cartilage defect 14, remains unchanged in its implanted position. Therefore, the cartilage surface 32, which forms a joint surface of the bone 18, also remains intact after resorption of the cell carrier layer 44 has started, differently from the case with implants known from the prior art as shown in FIG. 1. Contraction gaps do arise between units 46 in the edge area of the cartilage replacement implant 40 and result from machining smooth cartilage edges 26 of the intact cartilage area 16, but are so small that they do not form a point of attack, i.e., a biomechanical weak point.

If, prior to implantation, the cell carrier layer 44 was inoculated with cells, for example, chondrocytes cultured and proliferated from the body's own cells, these can then build up a new layer of cartilage which fills out the space 24 entirely after complete resorption of the cell carrier layer 44 and the carrier layer 42.

FIG. 5 shows a second cartilage replacement implant, generally designated by reference numeral 40'. In its basic structure it is similar to the cartilage replacement implant 40, and, therefore, identical reference numerals with the addition of a prime "'" are used. It comprises a carrier layer 42', which rests with surface-to-surface contact on a cell carrier layer 44' and is joined to the latter. Differently from the cell carrier layer 44, the cell carrier layer 44' is not divided up into individual units 46, but remains in one piece. It is, however, also conceivable to provide the cell carrier layer 44' with cut gaps 48 so that individual units 46 are formed.

To fix the cartilage replacement implant 40' in place, a bone-contacting surface 54' of the cell carrier layer 44' is adhesively bonded to the surface 20 of the bone 18. Alternatively, only a ring surface of the carrier layer 42' resting against the healthy cartilage edge 26 is adhesively bonded to the cartilage edge 26. Alternatively or additionally, holding pins 70, which have a head 72 resting against the carrier surface 52', extend through the entire cartilage replacement implant 40' and are anchored in the bone 18, may be provided.

Alternatively or additionally, the bone replacement implant 40' may be sutured to the intact cartilage area 16 in the area of the cartilage edges 26. Resorbable threads 74 are used for this purpose, and the cartilage replacement implant 40' is fixed in place by appropriate formation of knots 76 at the cartilage surface 32 and the carrier surface 52'. It is preferable for both the adhesive and the holding pins 70 that are used to consist of a biocompatible resorbable material.

The holding pins 70, the described suture material and the adhesive may also be used together with the cartilage replacement implant 40.

What is claimed is:

1. Method for treating a traumatic or inflammatory degenerate cartilage defect in cartilage in the human body, wherein a cartilage replacement implant for the biological regeneration of a damaged cartilage area of articular cartilage in the human body is inserted into the cartilage defect, the cartilage replacement implant comprising a cell carrier which has a defect-contacting surface for placement on the damaged cartilage area and is formed and designed for colonization with human cells, and the cell carrier resting with surface-to-surface contact on a carrier having a pore width of 20 μm or less and being joined to the carrier at a cell carrier surface that faces away from the defect-contacting surface, wherein the pore width of the carrier substantially prevents perfusion of cells from outside the cartilage replacement implant into the cell carrier, and wherein the cartilage defect is a cartilage defect in the knee, in the intervertebral disc or in any other joint of the human body.

2. Method for treating a traumatic or inflammatory degenerate cartilage defect in cartilage in the human body, wherein a cartilage replacement implant for the biological regeneration of a damaged cartilage area of articular cartilage in the human body is inserted into the cartilage defect, the cartilage replacement implant comprising a cell carrier which has a defect-contacting surface for placement on the damaged cartilage area and is formed and designed for colonization with human cells, and the cell carrier resting with surface-to-surface contact on a carrier having a pore width of 20 μm or less and being joined to the carrier at a cell carrier surface that faces away from the defect-contacting surface, and wherein the cartilage replacement implant is implanted without previous colonization of the cell carrier or the carrier with cells so as to enable stem cells to bleed from the bone marrow into the cartilage replacement implant.

3. Method in accordance with claim 2, wherein prior to insertion of the cartilage replacement implant, a subchondral plate on the bone is perforated.

\* \* \* \* \*